United States Patent [19]

Sela et al.

[11] 4,263,279

[45] Apr. 21, 1981

[54] PHARMACEUTICALLY ACTIVE COMPOSITIONS CONTAINING ADRIAMYCIN AND DAUNOMYCIN

[75] Inventors: Michael Sela; Ruth Arnon; Esther Hurvitz, all of Rehovot; Ruth Maron, Tel Aviv; Ron Levy, Rehovot, all of Israel

[73] Assignee: Yeda Research & Development Co. Ltd, Rehovot, Israel

[21] Appl. No.: 927,051

[22] Filed: Jul. 24, 1978

Related U.S. Application Data

[62] Division of Ser. No. 605,870, Aug. 19, 1975, abandoned.

[51] Int. Cl.³ .................... A61K 31/705; C07H 15/24
[52] U.S. Cl. ...................................... 424/85; 424/180; 536/17 A
[58] Field of Search ............... 536/17 A, 17, 9, 53; 424/85, 180

[56] References Cited

U.S. PATENT DOCUMENTS

| | | | |
|---|---|---|---|
| 3,100,203 | 8/1963 | Borchert | 536/53 |
| 3,794,635 | 2/1974 | Evans | 536/9 |
| 3,803,124 | 4/1974 | Arcamone et al. | 536/17 A |
| 3,957,755 | 5/1976 | Jolles | 536/17 A |
| 4,093,607 | 6/1978 | Sela et al. | 424/85 |

OTHER PUBLICATIONS

O'Bryan et al., "Cancer," vol. 32, No. 1, pp. 1–8, Jul. 1973.
Frei, "Cancer," vol. 30, No. 6, pp. 1656–1661, Dec. 1972.
Johnson et al., "Cancer Treatment Reviews," pp. 1–31, 1975.
Levy et al., "Cancer Research," vol. 35, pp. 1182–1185, 1975.
Hurwitz et al., "Cancer Res.," vol. 35, pp. 1175–1181, 1975.
Hurwitz et al., "Cancer, Europ. J.," vol. 14, pp. 1213–1220, 1978.

*Primary Examiner*—Johnnie R. Brown
*Attorney, Agent, or Firm*—Browdy and Neimark

[57] ABSTRACT

Novel pharmaceutically active compositions of matter comprise in combination a low-molecular-weight anticancer drug chemically linked to antibodies selective or specific to tumor antigens. The preferred linkage is via covalent bonds, whether directly or via a linking agent. A method of treatment of mammals afflicted with malignant growth comprises administering a pharmaceutical composition of matter defined above.

4 Claims, No Drawings

PHARMACEUTICALLY ACTIVE COMPOSITIONS CONTAINING ADRIAMYCIN AND DAUNOMYCIN

This is a division, of application Ser. No. 605,870 filed Aug. 19, 1975, now abandoned.

BACKGROUND OF THE INVENTION

Several anti-cancer drugs have attained a certain degree of success during recent years. Amongst these there may be specifically mentioned compounds such as daunomycin, adriamycin, methotrexate, mithramycin, cytosine arabinoside, 6-azauridine and the like. All these are low-molecular-weight compounds and these can be conjugated to form novel drugs according to the present invention.

One of the drawbacks of such anti-cancer drugs is a comparatively high degree of toxicity of same. Thus it is hard in some cases to use adequate dosages as these are too toxic to the mammal being treated.

During recent years various attempts have been made to prepare specific antibodies towards tumors, but these have not given hitherto the desired anti-cancer effects. Certain antibodies selective to tumors have been complexed in a non-covalent manner to antitumor drugs in order to enhance the effectiveness of such drugs against tumor cells. These too have not given the desired results.

SUMMARY OF THE PRESENT INVENTION

The present invention relates to novel pharmaceutically active compositions of matter. More particularly, the present invention relates to novel compositions of matter comprising low-molecular-weight anti-cancer drugs chemically linked to antibodies selective or specific to tumor antigens. The present invention also relates to pharmaceutical compositions of matter for use in the treatment of mammals afflicted with various types of malignant growths, comprising as active ingredient the novel compositions of matter according to the present invention. Other and further aspects of the invention will become apparent hereinafter.

According to the present invention specific cytotoxic effects can be attained by resorting to novel compositions of matter comprising anti-cancer drugs bound covalently to antibodies selective or specific to tumor antigens.

The antibodies are chosen according to the specific cytotoxic effect desired. Experiments have shown that a variety of tumor-specific antibodies can be effectively chemically linked to anti-cancer drugs. The latter are generally compounds of a comparatively low molecular weight. The antibodies are of a much higher molecular weight, mostly of the order of about 150,000, or a multiple (five units) of this molecular weight.

The effectiveness of the resulting composition of matter depends to a large extent on the nature of the chemical bond used. This has to be adjusted from case to case, and it is clear that in both components functional groups have to be chosen which are not necessary for the activity of the component. The anti-cancer drug may be chemically bound to the antibody either directly, or via a linking agent, such as a bivalent linking agent of the type of glutaralddehyde or the like.

When the direct linkage is resorted to, this can be effected by various chemical processes, such as the opening of a bond within the small molecule (generally the anti-cancer drug), and linking it to the antibody. The methods of linking desired chemical compounds to antibodies are quite well-known from literature. It is emphasized that in the preparation of compositions of matter according to the present invention the method of chemical linkage must be chosen in a careful manner, as great differences result from varying procedures. It has been found that the specificity of the antibodies to tumor antigens can be maintained in the final product. Furthermore, the specificity of the antibodies results in a substantial concentration of the novel products in the tumors or their immediate vicinity, enhancing the resultant effects and substantially decreasing the overall dosage necessary for cytotoxic effects. Thus, in certain cases where no adequate dosage of antitumor drugs could hitherto be used, this becomes possible by means of the novel products of the present invention.

With daunomycin and with adriamycin, the method of choice of linkage to specific immunoglobulins is the periodate oxidation of the drug, followed by the linking of the oxidized drug to the immunoglobulin, followed by the stabilization of the resulting bond through the reduction of the product with a suitable reducing agent, such as sodium borohydride. With methotrexate the method of choice was a linkage in the presence of 1-ethyl-3-(3-dimethylaminopropyl) carbodiimide hydrochloride with a suitable antibody.

The novel drugs according to the present invention can be used against a wide variety of tumors, against which the anti-cancer drugs forming part thereof are nowadays used.

Any suitable warm-blooded animal can be used for the production of the antibodies. For example, there may be used any of the conventional laboratory animals, such as rabbits, rats, dogs, etc. There may be used larger animals, such as rabbits, horses, goats and the like. Such antibodies are chemically bonded to the desired specific drug and formulated into pharmaceutical preparations by conventional techniques. The production of such antibodies is carried out according to conventional techniques, and these are well known to persons versed in the art.

Various types of bonding may be utilized. The preferred are chemical bonds of the covalent bond type. These may be either direct bonds, or they may be effected via suitable bivalent or other linking agents. The covalent bonds are stable ones, and such bonds are also stable inside the body of the animal treated.

The noval drugs are advantageously administered by injection. The dosage has to be varied according to the type of drug used and according to the specific use. With various laboratory animals it was found that an average dosage of about 1 to 5 mg of drug-antibody conjugate was necessary for achieving significant curative results. The drug-antibody conjugates are prepared in the form of conventional injectable pharmaceutical compositions of matter, with suitable adjuvants and/or carriers.

DESCRIPTION OF THE PREFERRED EMBODIMENTS

Daunomycin and adriamycin were covalently bound to immunoglobulin isolated from specific antitumor sera by periodate oxidation, presumably cleaving the bond between $C_3$ and $C_4$ of the amino-sugar moiety of the molecule, resulting in the formation of carbonyl groups capable of reacting with free amino groups of the protein, and the resulting Schiff base linkage was reduced with sodium borohydride. About 40 mg/ml of the drug, in 1 ml PBS, was mixed with a slight molar excess of 0.1 M sodium periodate and incubated for about 1 hour in the dark at ambient temperature. 1 M glycerol was added to a final concentration of 0.05 M to consume excess of periodate. The solution of the oxidized material was mixed with 1 ml of tumor-specific immunoglobulin, 20–25 mg/ml of 0.15 M potassium carbonate buffer, pH 9.5 and incubated again for 1 hour at ambient temperature. Sodium borohydride was added to a final concentration of 0.3 mg/ml, and the reaction was allowed to proceed for 2 hours at 37° C. Free and bound drugs were separated by gel filtration chromatography, using Bio-Gel P-100 or Sepharose 6B. Small quantities of the free drug were removed from the protein fractions by adsorption chromatography on Poropak Q. The portein-bound drugs passed through the column unretarded. About 2 to 5 moles drug per mole of antibody were bonded covalently.

Conjugates were prepared with various immunoglobulins, specific to various tumors. Amongst these were three mouse lymphoid tumors. The conjugates were tested for their toxic effects on various tumor target cells, measured by the inhibition of RNA synthesis or by their reduction of the growth of the tumor cells after transplantation. The novel drugs according to the present invention preferentially attack target cells recognizable by the antibody part of the drug conjugate.

Tumors. Several murine lymphoid tumors were used in this study. These include a carcinogen-induced B cell leukemia in SJL/J mice (Nature 241 (1973) 396), a Moloney virus induced lymphoma (YAC) in A/J mice (J. Nat. Canc. Inst. 32 (1964) 547) and a mineral oil induced plasmacytoma (PC5) in BALB/c mice (J. Nat. Canc. Inst. 25 (1960) 847). In addition a lymphoma induced in Lewis rats by the intrathymic injection of murine radiation leukemia virus was also used. This rat lymphoma shares viral related cell surface antigens with the PC5 plasmacytoma but not with the other mouse tumors employed here. All tumors were maintained by passage in their respective inbred animal strains.

Antisera. Antiserum to bovine serum albumin (anti-BSA) was produced in rabbits by weekly subcutaneous injection of 2 mg BSA emulsified in complete Freund's adjuvant.

Rabbit antisera to the B leukemia cells and to the PC5 cells were prepared by 4–5 intravenous injections of $10^8$ tumor cells at 5-day intervals. Antibody activity was measured by complement-dependent cytotoxicity as previously described*. Titers of 1/100 to 1/200 were obtained for these antisera against their respective immunizing cells. The anti-B-leukemia antisera showed similar cytotoxicity against the YAC tumor cells. The anti-PC5 antisera were used after absorption with normal BALB/c thymus and spleen cells, and in the absorbed form were cytotoxic against both the immunizing PC5 cells and the rat lymphoma cells, but not against the YAC cells.
*Cancer Research 35, 1175 (1975).

The immunoglobulin fractions of these antisera were prepared by precipitation with ammonium sulfate at 33% saturation, and used for the preparation of drug conjugates.

Drug Activity. The pharmacologic activity of daunomycin and adriamycin was measured primarily by their inhibition of cellular RNA synthesis. The assays were carried out in microtiter plates (Cooke, V bottom plates) in Eagles's minimal essential medium containing penicillin and streptomycin. Cells were suspended in medium at a concentration of $2 \times 10^7$ cells/ml and dispended into the wells of the plates in 50 μl aliquots. Drugs were diluted in PBS (0.15 M NaCl—0.01 M $PO_4$, pH 7.2) and then added to the cells in 50 μl amounts. The plates were incubated for 2 hours (unless otherwise stated in the text) at 37° C. in a humidified atmosphere of 5% $CO_2$ in air. At that time 10 μl containing 1 μc of 5-[$^3$H]uridine was added to each well and, after another 1–2 hours of incubation, 25 μl of 25% trichloroacetic acid (TCA) was added and the plates were placed at 4° C. overnight. TCA precipitates were washed, solubilized in NaOH, and transferred to vials for counting as described in Transplantation 13 (1972) 541-5. The scintillation mixture consisted of a toluene based scintillation solution, triton x-100, 0.1 N HCl in the proportions of 6/3/1. The HCl was included to counteract chemiluminescence. Assays were performed in triplicate, which generally has less than 10% variation. The experiments demonstrated that drug activity was retained after the conjugation to the antibody molecules, as shown in Table 1.

TABLE 1

Cytotoxic activity of drug-conjugates compared to free drug

| Incubation Time (min) | % Inhibition of [$^3$H] uridine incorporation | | |
|---|---|---|---|
| | Free daunomycin | Bound daunomycin | |
| | | Daunomycin-anti BSA | Daunomycin-anti B leukemia |
| 30 | 43 | 20 | 25 |
| 60 | 58 | 35 | 35 |
| 90 | 61 | 39 | 48 |
| 120 | 66 | 53 | 57 |
| 240 | 83 | 76 | 89 |

$10^7$ B leukemia cells were incubated at 37° C. in the presence of 4 μg/ml of daunomycin, either free or protein-bound. Incorporation of [$^3$H] uridine into cellular material precipitable by TCA was measured and expressed as percent inhibition (100-percent of control culture, containing no drug).

Pharmacologic Effects of the Drug Conjugates. The specific cytotoxicity of drug-immunoglobulin conjugates was tested after allowing them to attach to target cells during a short incubation in vitro, washing to remove non-specific proteins and their drug conjugates, and examining the cells for residual drug effects. Tumor cells were washed and suspended in Eagle's medium at a concentration of $2 \times 10^7$ cells/ml, and dispensed into the wells of microtiter plates (Cook, V bottom plates) in 50 μl volumes. Various concentrations of free drug, immunoglobulins or drug-immunoglobulin conjugates were added in 50 μl volumes, and after agitation (Cook AM 69 microshaker) the plates were incubated for 5 minutes at 37° C. One hundred μl of medium was then added to each well, and the plates were centrifuged at 4° C. at 1800 rpm (International PR-J centrifuge equipped with Cook plate carriers) for 10 minutes. Supernatants were removed by a single shake of the inverted plates, and the wells were refilled with 200 μl of fresh medium. This washing procedure was repeated one more time, and the cells were finally resuspended in Eagle's medium, 100 μl/well, and incubated for 2 hours at 37° C. in a humidified atmosphere of 5% $CO_2$ in air. Ten μl containing 1 μCi of [$^3$H]uridine was then added to each well, and after a further 1 hour incubation 25 μl of 25% TCA was added. TCA precipitates were washed, solubilized in NaOH, and counted for radioactivity as described by Rosenberg et al., Transplantation 13 (1972) 541-5. The results are expressed as percent inhibition of [$^3$H]uridine incorporation, compared to the control which contained either saline or free antibody at a concentration equivalent to the antibody concentration of the corresponding cojugate. The variation of triplicates in this assay was generally less than 10%.

In addition to the [³H]uridine incorporation assay, the target tumor cells were tested for their ability to grow after transplantation. After exposure to the drug conjugates in vitro and washing, the cells were transplanted into their respective syngeneic strains, and the survival of recipients was followed.

Specific Cytotoxicity of Daunomycin Anti-B-leukemia Conjuages

Daunomycin was conjugated both to anti-B-leukemia and anti-BSA immunoglobulins, and tested for cytotoxicity against the B leukemia cells as well as several other tumors in vitro. These conjugates retained appropximately 50% of the activity of the free drug. The different tumors used here had similar sensitivities to the drug immunoglobulin conjugates. For the present experiments a concentration of daunomycin-immunoglobulin conjugate was used which gave 40-60% inhibition of [³H]uridine incorporation in test cells when it was left in contact with the target cells for the entire period of the incubation. To reveal the specificity of the conjugates, the test cells were exposed to them for only 5 minutes, to allow attachment of specific antibody, then washed to remove non-specific immunoglobulins, and the toxicity of the daunomycin remaining in contact with the cells was assessed as described above.

From the results shown in Table 2, it can be seen that the daunomycin-anti-B-leukemia conjugate showed significant residual inhibition of [³H]uridine incorporation in the B-leukemia cells after this brief exposure and washing. When different target cells were tested in this assay we found that their sensitivity to the specific daunomycin-anti-B-leukemia conjugate followed the specificity of the antibody. That is, this conjugate was toxic to the cross-reacting YAC cells but not to the non-cross-reacting PC5 or rat lymphoma cells (line 1), even though the sensitivity of these cells to the free drug was, if anything, greater than that of the B leukemia cells (line 4). The specific effect observed here depended upon the antibody activity since no effect was seen with the daunomycin-anti-BSA conjugate (line 2). In the case of the B leukemia test cells, the effect of the daunomycin-antibody conjugate was even greater than that of the free drug (line 4, column 1). Free antibody did not render the cell more sensitive to the effects of the free drug (data not shown), but increased slightly the effect of the non-specific daunomycin-anti-BSA conjugate on these cells (column 1, line 3). The heavy agglutination of the cells caused by the antibody may have resulted in some trapping of the daunomycin anti-BSA conjugate making it more difficult to remove by washing. YAC cells, which were not strongly agglutinated by the anti-B-leukemia antibodies were not affected by the mixture of anti-B-leukemia and daunomycin-anti-BSA (line 3, column 2).

TABLE 2

| | Specific cytoxicity of daunomycin linked to anti-B-leukemia | | | | |
|---|---|---|---|---|---|
| | % Inhibition of [³H]uridine incorporation[a] Test cells | | | | Mean survival |
| Incubated with | B leukemia | YAC | PC5 | Rat lymphoma | time (days)[b] |
| Daunomycin-anti- | | | | | |
| B-leukemia | 38[a] | 42[a] | 17[b] | 9[b] | 19.4 |
| Daunomycin-anti-BSA | 1[b] | 0[b] | 4 | 9 | 12.2 |
| Daunomycin-anti-BSA + anti-B-leukemia | 18[c] | 0[d] | N.D. | N.D. | 12.2 |
| Free daunomycin | 17 | 49 | 33 | 41 | 10.7 |
| PBS | | | | | 11.3 |

[a]0.6 μg drug either as the protein conjugate or free drug was incubated with 10⁶ cells in a total volume of 100 μl for 5 minutes at 37° C. Medium was then removed, cells were washed and resuspended in fresh medium and pulsed with [³H]uridine at the end of two hours of further incubation.
Differences betweem [a] and [b] p < .001 by the Student's T Test.
Difference between [a] and [c] p < .05.
Difference between [a] and [d] p < .001.
[b]Animals were injected with 10⁷ cells which were previously treated by brief exposure to the various drug-conjugates.

In addition to their effects on RNA synthesis, the conjugates were tested for their effects on tumor cell growth. After brief exposure of the B leukemia cells in vitro to the conjugates, free antibodies or free drug, they were washed and transplanted in the syngeneic SJL/J host. (Table 2, last column). The mean survival of animals receiving untreated cells was 11 days. None of the other control groups, which received cells exposed to free drug, free antibody or the mixture of anti-B-leukemia antibody and daunomycin-anti-BSA, differed in their survival from those receiving untreated cells. Only the group receiving cells exposed to the specific daunomycin-anti-B-leukemia conjugate showed prolonged survival. Their survival was equivalent to that of animals receiving only 10³ untreated cells.

Specific Cytotoxic Effects of Daunomycin-anti-PC5 Conjugates. Similar experiments were performed using daunomycin conjugated to anti-PC5 immunoglobulins. Once again it can be seen (Table 3) that the specific conjugate showed toxicity against the homologous PC5 target cell and against the cross-reacting rat lymphoma cells, but much less against the non-cross-reacting YAC cells. In this series of experiments the daunomycin-anti-B-leukemia conjugate was included as a specificity control, showing the converse pattern of toxic effects. Again, the homologous system, daunomycin-anti-PC5 against the PC5 test cell, was even superior to the effect of free drug on the same cells.

When the growth of the treated PC5 cells was examined in syngeneic BALB/c animals, we found a slight effect of free drug as well as of free antibody, but the specific daunomycin-anti-PC5 conjugates resulted in an even greater effect, including failure of tumor take in over 50% of the animals (last column of Table 3). The survival of this group of animals was equivalent to animals receiving only 10² untreated tumor cells.

TABLE 3

| | Specific cytotoxicity of daunomycin linked to anti-PC5 immunoglobulins | | | |
|---|---|---|---|---|
| | % Inhibition of [³H]uridine incorporation[a] Test cells | | | Mean survival |
| Incubated with | PC5 | Rat lymphoma | YAC | time |
| Daunomycin-anti-RPC5 | 60[a] | 63[a] | 20[b] | 3 mice >60 2 mice 27.5 |

TABLE 3-continued

Specific cytotoxicity of
daunomycin linked to anti-PC5 immunoglobulins

| Incubated with | % Inhibition of [³H]uridine incorporation[a] Test cells | | | Mean survival time |
| --- | --- | --- | --- | --- |
| | PC5 | Rat lymphoma | YAC | |
| Daunomycin-anti-BSA | 7[b] | 14[b] | N.D. | 19.8 |
| Daunomycin-anti-B-leukemia | 16[b] | 14[b] | 62[a] | |
| Free daunomycin | 32[c] | 53 | 67 | 25.6 |
| PBS | | | | 21 |

[a] 1.5 μg of drug was used, other conditions were identical to those in Table 1. All [a] different from all [b] by $p < .001$, Student's T test.
[a] different from [c] by $p < .001$.
[b] Animals were injected with $10^7$ cells which were previously treated by brief exposure to the various drug conjugates.

The long term survivors were resistant to subsequent challenge with $10^3$ tumor cells.

In an additional series of experiments, the cells were treated briefly in vitro as before, but transplanted without washing, relying on dissipation of drug and nonspecific drug conjugates in the animal. The results are similar. An additional control group in which cells were exposed to a mixture of free drug and anti-PC5 antibody, resulted in no apparent effect over that of either the free drug or the free antibody alone.

In the present series of experiments it was shown that daunomycin covalently bound to antibodies directed against individual tumors showed preferential cytotoxicity against these specific tumor cells. When the drug was bound to anti-B-leukemia antibodies, the conjugates were toxic to the homologous B leukemia cells as well as to the cross-reacting YAC cells (Table 2), but were not significantly toxic to the non cross-reacting PC5 or rat lymphoma cells (Tables 2 and 3).

We claim:

1. A compound consisting of daunomycin or adriamycin covalently bonded to an antibody selective or specific to the antigen of a tumor against which tumor the daunomycin or adriamycin is effective, wherein the functional groups of the daunomycin or adriamycin and of the antibody which are reacted to form the covalent linkage of the daunomycin or adriamycin and the antibody are ones which are not necessary for the pharmaceutical activity of the daunomycin or adriamycin or the selectivity or specificity of the antibody.

2. A compound in accordance with claim 1, wherein the bonding is via the amino-sugar moiety of the daunomycin or adriamycin.

3. A compound in accordance with claim 1, wherein there are bonded about 2 to 10 molecules of daunomycin or adriamycin per molecule of said antibody.

4. A pharmaceutical composition, in injectable form, containing from 50 mg to 500 mg of the compound of claim 1 in a pharmaceutically acceptable carrier.

* * * * *